United States Patent
Bolea

(10) Patent No.: US 8,417,014 B2
(45) Date of Patent: Apr. 9, 2013

(54) SPECTRAL ANALYSIS OF BIOLOGICAL GROWTH MEDIA

(75) Inventor: Phillip A. Bolea, Grant, MN (US)

(73) Assignee: 3M Innovative Properties Company, St. Paul, MN (US)

(*) Notice: Subject to any disclaimer, the term of this patent is extended or adjusted under 35 U.S.C. 154(b) by 0 days.

(21) Appl. No.: 12/921,418

(22) PCT Filed: Mar. 17, 2009

(86) PCT No.: PCT/US2009/037359
§ 371 (c)(1),
(2), (4) Date: Mar. 7, 2011

(87) PCT Pub. No.: WO2009/120532
PCT Pub. Date: Oct. 1, 2009

(65) Prior Publication Data
US 2011/0150314 A1 Jun. 23, 2011

Related U.S. Application Data

(60) Provisional application No. 61/039,453, filed on Mar. 26, 2008.

(51) Int. Cl.
*G06K 9/00* (2006.01)
*G01B 9/02* (2006.01)
(52) U.S. Cl. .......................... 382/133; 382/274; 356/484
(58) Field of Classification Search .................. 382/100, 382/103, 107, 128–134, 162, 168, 173, 181, 382/199, 203, 207, 209, 224, 232, 254, 276, 382/291, 305, 312, 274; 435/6.12, 286.2; 119/174; 356/301, 484
See application file for complete search history.

(56) References Cited

U.S. PATENT DOCUMENTS

| | | | |
|---|---|---|---|
| 5,403,722 A | 4/1995 | Floeder et al. | 435/39 |
| 6,063,590 A | 5/2000 | Brenner et al. | 435/29 |
| 7,057,721 B2 * | 6/2006 | Gardner et al. | 356/301 |
| 7,298,885 B2 * | 11/2007 | Green et al. | 382/133 |
| 7,351,574 B2 * | 4/2008 | Vent | 435/286.2 |
| 7,496,225 B2 * | 2/2009 | Graessle et al. | 382/133 |
| 7,865,008 B2 * | 1/2011 | Graessle et al. | 382/133 |
| 8,097,416 B2 * | 1/2012 | Hall et al. | 435/6.12 |
| 8,256,381 B2 * | 9/2012 | Pratt | 119/174 |
| 2004/0101951 A1 | 5/2004 | Vent et al. | 435/287 |
| 2004/0101954 A1 | 5/2004 | Graessle et al. | 435/288 |
| 2004/0102903 A1 | 5/2004 | Graessle et al. | 702/19 |
| 2005/0053265 A1 | 3/2005 | Graessle et al. | 382/128 |
| 2005/0053266 A1 | 3/2005 | Plumb et al. | 382/128 |
| 2005/0185178 A1 | 8/2005 | Gardner, Jr. et al. | 356/301 |

OTHER PUBLICATIONS

Kalasinsky, K. et al.; "Raman Chemical Imaging Spectroscopy Reagentless Detection and Identification of Pathogens: Signature Development and Evaluation"; Analytical Chemistry; vol. 79; No. 7; 2007; pp. 2658-2673.

* cited by examiner

*Primary Examiner* — Seyed Azarian

(57) ABSTRACT

This disclosure is directed to imaging techniques and image analysis techniques for automated analysis of biological growth media. According to this disclosure, the spectral responses of biological growth media can be used to identify and count biological agents from images of biological growth media. The biological growth media may be illuminated with two or more different wavelengths of electromagnetic radiation, and images of the biological growth media can be captured under these different illuminations. The spectral reflectance values in one or more first images can be normalized based on the spectral reflectance values in one or more second images, wherein the first images are associated with a different wavelength of illumination than the second images. The normalization may allow for better identification of biological agents that manifest on the biological growth media.

13 Claims, 8 Drawing Sheets

SPECTRAL ANALYSIS OF BIOLOGICAL GROWTH MEDIA

CROSS REFERENCE TO RELATED APPLICATIONS

This application claims the benefit of U.S. Provisional Application Ser. No. 61/039,453, filed Mar. 26, 2008, which is incorporated herein by reference.

BACKGROUND

Biological safety is a paramount concern in modern society. Testing for biological contamination in foods or other materials has become an important and sometimes mandatory requirement for developers and distributors of food products. Biological testing is also used to identify bacteria or other agents in laboratory samples such as blood samples taken from medical patients, laboratory samples developed for experimental purposes, and other types of biological samples. Various techniques and devices can be utilized to improve biological testing and to streamline and standardize the biological testing process.

In particular, a wide variety of biological growth media have been developed. As one example, biological growth media in the form of growth plates have been developed by 3M Company (hereafter "3M") of St. Paul, Minn. Biological growth plates are sold by 3M under the trade name PETRIFILM plates. Biological growth plates can be utilized to facilitate the rapid growth and detection or enumeration of bacteria or other biological agents commonly associated with food contamination, including, for example, aerobic bacteria, E. coli, coliform, Enterobacteriaceae, yeast, mold, Staphylococcus aureus, Listeria, Campylobacter, and other biological agents. The use of PETRIFILM plates, or other biological growth media, can simplify bacterial testing of food samples.

Biological growth media can be used to identify the presence of bacteria so that corrective measures can be performed (in the case of food testing) or proper diagnosis can be made (in the case of medical use). In other applications, biological growth media may be used to rapidly grow bacteria or other biological agents in laboratory samples, e.g., for experimental purposes.

Biological growth medium processing systems refer to systems used to process biological growth media. Biological growth medium processing systems may be used enumerate bacterial colonies, or the amount of a particular biological agent on a biological growth medium. For example, a food sample or laboratory sample can be placed on a biological growth medium, and then the medium can be inserted into an incubation chamber. After incubation, the biological growth medium can be introduced into a biological reader, which generates one or more images of the biological growth medium. The images can then be analyzed, e.g., via a computer, for automated enumeration of bacterial growth. In this way, biological growth medium processing systems automate the detection and enumeration of bacteria or other biological agents on a biological growth medium, and thereby improve the biological testing process by reducing human error.

SUMMARY

In general, this disclosure is directed to imaging techniques and image analysis techniques for automated analysis of biological growth media. According to this disclosure, the spectral responses of biological growth media can be used to identify and count biological agents from images of biological growth media. The biological growth media may be illuminated with two or more different wavelengths of electromagnetic radiation, and images of the biological growth media can be captured under these different illuminations. The spectral reflectance values in one or more first images (e.g., associated with pixel locations) can be normalized based on the spectral reflectance values in one or more second images (e.g., associated with the same pixel locations). In this case, the first images are associated with a different wavelength of illumination than the second images. The normalization may allow for better identification of biological agents that manifest on the biological growth media. In this way, spectral analysis and normalization may improve automated detection of biological agents.

The first images may be generated under an illumination of light in a first range of wavelengths, and the second images may be generated under illumination of light in a second range of wavelengths. The spectral response of biological agents and the spectral response of the background may differ in the different ranges of wavelengths. The second images can be used to normalize the first images, which may improve the ability to distinguish the background of the biological media from biological agents that manifest on the media. The illumination used for the first images may be within a visible spectrum, and the illumination used for the second images may be outside the visible spectrum.

In one embodiment, this disclosure provides a method comprising illuminating a biological growth medium with electromagnetic radiation that is outside a visible spectrum, generating one or more images of the biological growth medium illuminated with the electromagnetic radiation outside the visible spectrum; and counting biological agents on the biological growth medium based on the one or more images.

In another embodiment, this disclosure provides a method comprising illuminating a biological growth medium with first electromagnetic radiation, generating one or more first images of the biological growth medium illuminated with the first electromagnetic radiation, illuminating the biological growth medium with second electromagnetic radiation, generating one or more second images of the biological growth medium illuminated with the second electromagnetic radiation, normalizing spectral reflectance values in the one or more first images based on the one or more second images, identifying the biological agents based on the normalized spectral reflectance values, and counting the identified biological agents.

In another embodiment, this disclosure provides a system comprising an imaging unit that illuminates a biological growth medium with electromagnetic radiation that is outside a visible spectrum, and generates one or more images of the biological growth medium illuminated with the electromagnetic radiation outside the visible spectrum, and a computer that counts the biological agents on the biological growth medium based on the one or more images.

In another embodiment, this disclosure provides a system comprising an imaging unit that illuminates a biological growth medium with first electromagnetic radiation, generates one or more first images of the biological growth medium illuminated with the first electromagnetic radiation, illuminates the biological growth medium with second electromagnetic radiation, and generates one or more second images of the biological growth medium illuminated with the second electromagnetic radiation. The system also includes a computer that normalizes spectral reflectance values in the one or more first images based on the one or more second images, identifies the biological agents based on the normalized spectral reflectance values, and counts the identified biological agents.

In another embodiment, this disclosure provides a system comprising means for illuminating a biological growth medium with electromagnetic radiation that is outside a visible spectrum, means for generating one or more images of the biological growth medium illuminated with the electromagnetic radiation outside the visible spectrum, and means for counting biological agents on the biological growth medium based on the one or more images.

In another embodiment, this disclosure provides a system comprising means for illuminating a biological growth medium with first electromagnetic radiation, means for generating one or more first images of the biological growth medium illuminated with the first electromagnetic radiation, means for illuminating the biological growth medium with second electromagnetic radiation, means for generating one or more second images of the biological growth medium illuminated with the second electromagnetic radiation, means for normalizing spectral reflectance values in the one or more first images based on the one or more second images, means for identifying the biological agents based on the normalized spectral reflectance values, and means for counting the identified biological agents.

In another embodiment, this disclosure provides a computer-readable medium comprising instructions that upon execution in a computer of a biological growth medium processing system cause the computer to receive one or more images of the biological growth medium, the one or more images having been generated during illumination of the biological growth medium with the electromagnetic radiation outside the visible spectrum, and count biological agents on the biological growth medium based on the one or more images.

In another embodiment, this disclosure provides a computer-readable medium comprising instructions that upon execution in a computer of a biological growth medium processing system cause the computer to receive one or more first images of the biological growth medium, the one or more first images having been generated during illumination of the biological growth medium with first electromagnetic radiation, receive one or more second images of the biological growth medium, the one or more second images having been generated during illumination of the biological growth medium with second electromagnetic radiation, normalize spectral reflectance values in the one or more first images based on the one or more second images, identify the biological agents based on the normalized spectral reflectance values, and count the identified biological agents.

Additional details of these and other embodiments are set forth in the accompanying drawings and the description below. Other features, objects and advantages will become apparent from the description and drawings, and from the claims.

DETAILED DESCRIPTION

This disclosure is directed to imaging techniques and image analysis techniques for automated analysis of biological growth media. Biological growth media comprise at least one nutrient to support the growth of microorganisms and, optionally, may comprise at least one indicator to facilitate the detection of a specific microorganism or group of microorganisms. According to this disclosure, measured spectral reflectance values of biological growth media can be used to identify and count biological agents from images of biological growth media. In particular, spectral reflectance values of the biological growth media in two or more different wavelength ranges may be used to identify and count biological agents.

The biological growth media may be illuminated with two or more different wavelengths of electromagnetic radiation, and images of the biological growth media can be captured under these different illuminations. The spectral reflectance values in one or more first images can be normalized based on the spectral reflectance values in one or more second images in order to better identify biological agents that manifest on the biological growth media. For example, the spectral reflectance value of a first image at a specific pixel location can be normalized based on the spectral reflectance values in one or more second images at that same pixel location. The normalization may use ratios, in which case, ratios of the spectral reflectance values at pixel locations in first images to the spectral reflectance values at the same pixel locations in second images can be used to identify the biological agents and to identify background areas of the biological growth media. In this way, spectral analysis may improve automated detection of biological agents.

The first images may be generated under an illumination of light in a first range of wavelengths, and the second images may be generated under illumination of light in a second range of wavelengths. The spectral response of biological agents relative and the background areas may differ in the different illuminations. According to this disclosure, the first images can be normalized based on the second images, thereby improving an ability to distinguish the background of the biological media from biological agents that manifest on the media. The spectral reflectance values associated with biological agents and with background areas may differ in the different wavelength ranges. Normalization techniques can exploit this observed phenomenon to improve enumeration of biological agents.

The illumination used for the first images may be within a visible spectrum, and the illumination used for the second images may be outside the visible spectrum. In this way, the spectral response of biological growth media over a broad range of wavelengths (both within the visible spectrum and outside the visible spectrum) may be exploited to improve automated readout of biological growth media.

Figure 1:
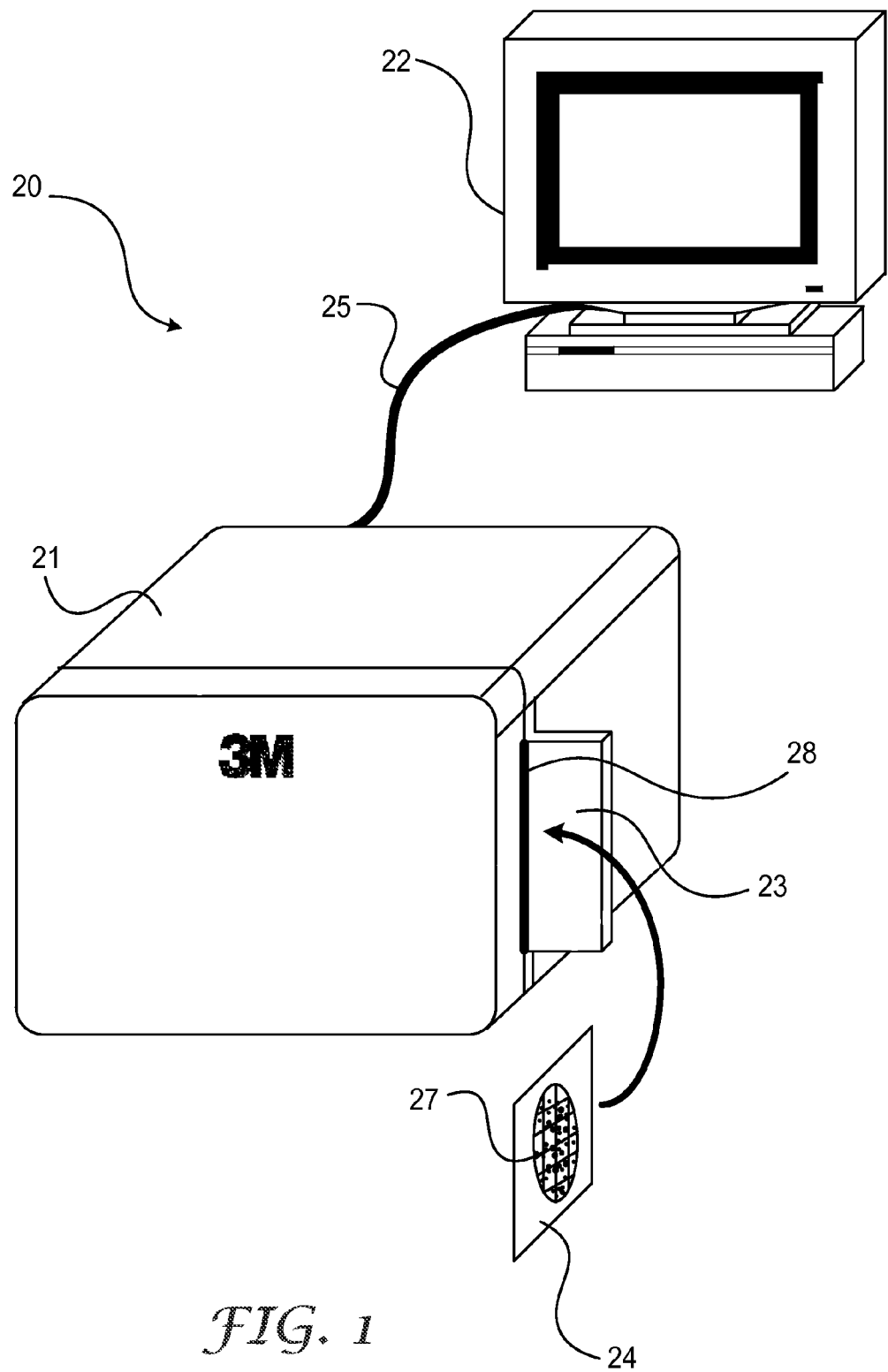
FIG. 1 is a perspective view of an exemplary biological growth medium processing system capable of implementing one or more of the techniques described herein during the processing of a biological growth medium.

FIG. 1 is a perspective view of an exemplary biological growth medium processing system 20 capable of implementing one or more of the techniques of this disclosure during the processing of biological growth medium 24. System 20 comprises an imaging unit 21 coupled to a computer 22. Imaging unit 21 captures images of biological growth medium 24 under two or more different illumination settings (e.g., under different wavelengths of illumination), and computer 22 processes the images to identify and count biological agents on biological growth medium 24. Alternatively, white light and color filters, or other techniques may be used to facilitate illumination at different wavelengths.

Although computer 22 and imaging unit 21 are illustrated as separate units, the techniques of this disclosure could also be implemented by a fully integrated system or device in which imaging unit 21 and computer 22 are incorporated into a common device, i.e., a fully integrated biological reader. Furthermore, the techniques of this disclosure could also be used in a modular system that includes one or more imaging units, one or more incubation units, one or more inoculation units, one or more identification element (ID) readers, ID labelers, and/or other devices that operate in a modular processing pipeline associated with biological growth medium 24.

Figure 2:
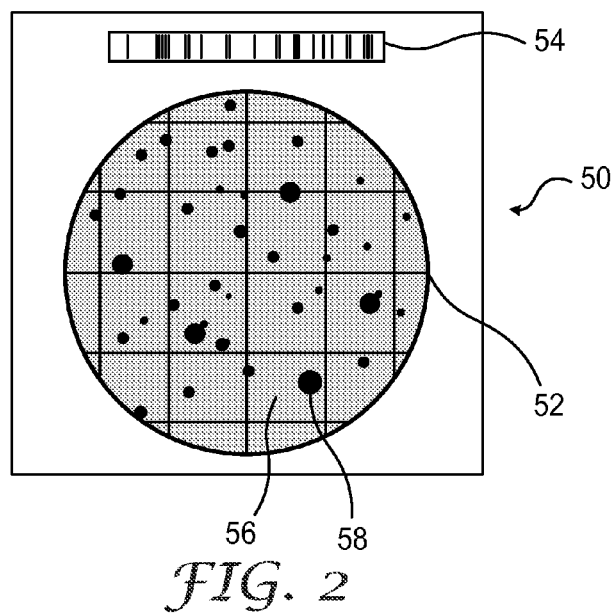
FIG. 2 is a top view of an exemplary biological growth media in the form of biological growth plate according to this disclosure.

If desired, imaging unit 21 may include an ID reader to read ID elements (not shown in FIG. 1) from biological growth medium 24. In this case, the ID elements may identify the plate type of biological growth medium 24 and allow computer 22 to select or adjust the image analysis based on the plate type. Furthermore, other types of information may also be coded or mapped to ID elements. FIG. 2 shows one exemplary biological growth plate that includes an ID element in the form of a bar code. FIG. 2 is discussed in greater detail below.

In the example of FIG. 1, computer 22 may include a microprocessor that executes software for image analysis of biological growth medium 24. Accordingly, computer 22 may also include memory to store various types of information, such as image analysis algorithms that execute techniques consistent with the teaching of this disclosure. By way of example, computer 22 may comprise a personal computer (PC), desktop computer, laptop computer, handheld computer, workstation, or the like. Software programs may be loaded on computer 22 to facilitate image analysis of images of biological growth medium 24 generated by imaging unit 21.

In the example of FIG. 1, imaging unit 21 is coupled to computer 22 via interface 25. Interface 25, for example, may comprise a Universal Serial Bus (USB) interface, a Universal Serial Bus 2 (USB2) interface, an IEEE 1394 FireWire interface, a Small Computer System Interface (SCSI) interface, an Advance Technology Attachment (ATA) interface, a serial ATA interface, a Peripheral Component Interconnect (PCI) interface, a serial or parallel interface, or the like.

Imaging unit 21 is designed to receive a biological growth medium 24. In particular, imaging unit 21 includes a housing that defines an input slot 28 for receiving biological growth medium 24. A guide mechanism 23 may be formed on the housing to aid insertion of biological growth medium 24 into imaging unit 21. Imaging unit 21 also includes an ejection slot (not shown), through which biological growth medium 24 is ejected following imaging of biological growth medium 24. Imaging unit 21 may also include other features, such as a display screen (not shown) to display the progress or results of analysis of the biological growth plate to a user. The techniques of this disclosure, however, could be used with a wide variety of other types of imaging devices.

Imaging unit 21 houses imaging components, such as illumination sources and one or more cameras. In one example, imaging unit 21 houses a 2-dimensional monochromatic camera for generating one or more monochromatic images of an inserted biological growth medium 24. The illumination sources in imaging unit 21 may provide for illumination in two or more different wavelengths of electromagnetic radiation. The illumination sources in imaging unit 21 may illuminate the front and/or back sides of biological growth medium 24 during imaging. The illuminators can illuminate biological growth medium 24 with two or more different wavelengths of light, and different images of biological growth medium 24 can be generated under the different wavelengths of illumination. A transparent platen may be housed within imaging unit 21 to define an imaging location for biological growth medium 24 relative to the camera. Imaging unit 21 may communicate the images to computer 22, which may include a processor for performing image analysis.

Biological growth medium 24 may include a growth area 27 where bacteria or other agents manifest on biological growth medium 24. Growth area 27 may comprise a flat surface, a recessed well or any surface useful for biological growth. Biological growth medium 24 may be manufactured to included nutrients in growth area 27 to facilitate the rapid growth of a particular biological agent. A sample (such as a food sample or laboratory sample) may be added to growth area along with one or more dilution agents, if desired. This process of adding a sample (and possibly a dilution agent) to growth area 27 is referred to as inoculation, and may be performed manually by a user, or automatically by an inoculation unit (not shown in FIG. 1). Following inoculation, biological growth medium 24 may then be incubated in an incubation chamber or unit (not shown in FIG. 1).

Following inoculation and incubation, biological growth medium 24 is processed by imaging unit 21 in order to generate images in the manner described herein. In particular, imaging unit 21 generates at least two different images under two different wavelengths of illumination light. The images are sent from imaging unit 21 to computer 22, which performs image analysis.

For example, imaging unit 21 may generate first images under an illumination of light in a first range of wavelengths. In addition, imaging unit 21 may generate second images under illumination of light in a second range of wavelengths. In this way, biological growth medium 24 is illuminated with two or more different wavelengths of electromagnetic radiation, and images of the biological growth media are captured by imaging unit 21 under these different illuminations.

In computer 22, the spectral reflectance values in one or more first images can be normalized based on the spectral reflectance values in one or more second images in order to better identify biological agents that manifest on the biological growth media. In other words, computer 22 uses ratios of the spectral reflectance values in first images to the spectral reflectance values in second images to identify the biological agents relative to a background of biological growth medium 24. In this way, computer 22 uses spectral analysis in the automated detection of biological agents. The spectral reflectance values may be given as percentages of reflectance of light at a particular wavelength, and may be associated with specific pixel locations (or specific areas) in the two different images.

The spectral responses of biological agents and the background may differ in the different ranges of wavelengths. Computer 22 can normalize reflectance values at pixel locations of the first images based on reflectance values at pixel locations in the second images, thereby improving an ability of computer 22 to distinguish the background of biological growth medium 24 from biological agents that manifest on the biological growth medium 24. The reflectance values may represent the spectral reflectance of biological growth medium 24 at a given location under the illumination associated with the different images.

The illumination used by imaging unit 21 for the first images may be within a visible spectrum, and the illumination used by imaging unit 21 for the second images may be outside the visible spectrum. In this way, the spectral response of biological growth medium 24 over a broad range of wavelengths (both within the visible spectrum and outside the visible spectrum) may be exploited to improve automated readout. The images may be generated when biological growth medium 24 is in a fixed location to ensure that the pixels of the different images accurately align for purposes of normalization.

A determination of whether a given sample being tested in biological growth medium 24 is acceptable, in terms of bacterial colony counts or other biological agents may depend on the number of bacterial colonies per unit area. Accordingly, images generated by imaging unit 21 can be analyzed by computer 22 and used to quantify the amount of bacterial colonies per unit area on biological growth medium 24. Moreover, the spectral analysis and normalization techniques described herein can improve the ability of computer 22 to distinguish bacterial colonies or other biological agents from background of biological growth medium 24. The size of individual colonies may also be factored into the analysis, if desired.

FIG. 2 is a top view of an exemplary biological growth medium in the form of a biological growth plate 50. By way of example, biological growth plate 50 may comprise biological growth plates sold by 3M under the trade name PETRI-FILM plates. In some cases, biological growth plate 50 may include an identification element 54 to facilitate automated processing of biological growth plate 50.

Identification element 54 is illustrated as an optically readable pattern, e.g., a bar code. In other cases, however, identification element 54 may assume a wide variety of optical patterns such as characters, bar codes, two-dimensional bar codes, optical gratings, holograms, phosphorous inks and the like. Moreover, in some embodiments, identification element 54 may comprise visible or non-visible circuits or magnetic elements, which may be readable by magnetic or radio frequency techniques. For example, identification element 54 may comprise any of a wide variety of radio frequency identification (RFID) tags commonly used in many industries for inventory tracking purposes.

Biological growth plate 50 may facilitate the rapid growth and detection and enumeration of bacteria or other biological agents including, for example, aerobic bacteria, *E. coli*, coliform, Enterobacteriaceae, yeast, mold, *Staphylococcus aureus, Listeria*, and *campylobacter*, and the like. The use of PETRIFILM plates, or other growth media, can simplify bacterial testing of food samples.

As shown in FIG. 2, biological growth plate 50 defines a growth area 52. A determination of whether a given sample being tested in plate 50 is acceptable, in terms of bacterial colony counts, may depend on the number of bacterial colonies per unit area. Accordingly, in accordance with this disclosure, an automated system may process biological growth plate 50 to quantify the amount of bacterial colonies per unit area on plates 50 and may compare the amount, or "count," to a threshold. The threshold may represent, for example, a colony count which relates to an acceptable (or unacceptable) number of microorganisms in the original sample. The surface of biological growth plate 50 may contain one or more growth enhancing agents designed to facilitate the rapid growth of one or more types of bacteria or other biological agents.

Biological growth plate 50 may be inoculated with a sample. Inoculation refers to the process of adding a sample of material being tested to the surface of biological growth plate 50 within growth area 52, possibly with a dilution agent. Inoculation may be performed manually or in an automated fashion. After inoculation, biological growth plate 50 can be inserted into an incubation chamber (not shown). In the incubation chamber, microorganisms such as bacteria, yeast, or mold grow on the nutrients in the biological growth plate 50 and, after a period of time, manifest themselves as colonies. The colonies (e.g., mold or other microorganisms), represented by various dots on biological growth plate 50 of FIG. 2, may appear in different colors relative to the background colors of growth area 52, facilitating automated detection and enumeration of bacterial colonies via image analysis techniques. In particular, area 58 associated with a biological agent may appear different than area 56 associated with a background of biological growth plate 50, particularly in the visible spectrum.

As described in this disclosure, two or more different images of biological growth plate 50 are generated. One or more first images may be generated under illumination by electromagnetic radiation in a first wavelength, e.g., light within the visible spectrum. One or more second images may be generated under illumination by electromagnetic radiation in a second wavelength, e.g., light outside the visible spectrum. The ratio of spectral reflectance at individual pixel locations in the second image relative to corresponding pixel locations of the first image can aid in detecting area 58 associated with a biological agent relative to area 56 associated with a background. Area-based comparisons of area 58 relative to area 56, or possibly pixel-based ratios for every pixel location, can be used to determine whether area 58 (or the pixels within area 58) indeed corresponds to a bacterial colony that has grown on biological growth plate 50.

In other words, a computer may calculate the ratio of reflectance values in the first images relative to the second images in area 58, and the ratio of reflectance values of the first images relative to the second images in area 56. These ratios may provide a more definite distinction between areas 58 and 56 than can be defined from one set of images alone. The process of defining theses ratios is referred to as normalization of the first images based on the second images. Such normalization can improve the ability to identify biological agents associated with area 58 relative to background associated with area 56. For example, at every pixel location (or possibly for sets of pixels within different areas), the ratios generated to normalize the first images may be compared to a threshold to determine whether that location corresponds to a biological agent or background. Other more complicated enumeration rules or techniques could also be applied to the calculated ratios at every pixel location (or at different areas defined by sets of pixel locations). The reflectance values may be measured in any type of units, and in some cases, may comprise unitless percentage values.

Figure 3:
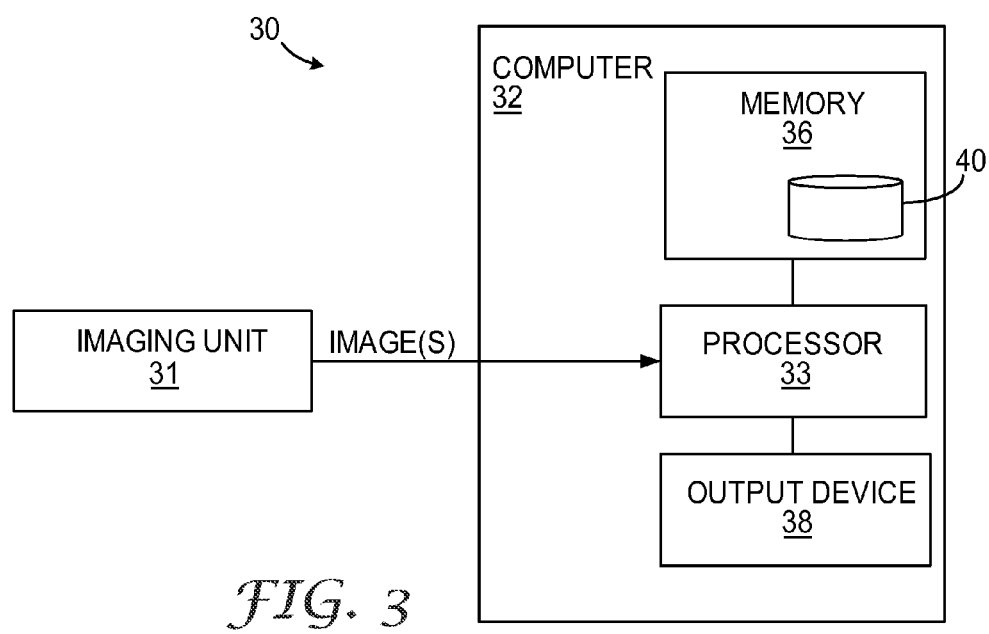
FIG. 3 is a block diagram of a biological growth medium processing system consistent with this disclosure.

FIG. 3 is a block diagram of a biological growth medium processing system 30, which may correspond to system 20 of FIG. 1 or another system, such as a fully integrated biological reader or a modular system. System 30 includes a computer 32, which may include a processor 33 coupled to memory 36. If desired, computer 32 may be coupled to an output device 38, such as a display screen. Computer 32 may also be coupled to other processing units (not shown) such as inoculation units, incubation units, ID readers, labeling devices, or the like.

Imaging unit 31 is coupled to computer 32. Imaging unit 31 generates one or more images of a biological growth medium and provides the images to computer 32. Processor 33 processes the images based on image analysis algorithms stored in memory 36. For example, memory 36 may store various processor-executable software instructions that facilitate image analysis of the images generated by imaging unit 31. Processor 33 executes such instructions to carry out the techniques of this disclosure. Output device 38 receives the results determined by processor 33 and provides the results to a user.

Memory 36 may also store a database 40, as well as database management software for the management of database 40. Database 40 of memory 36 can be used to associate the different types of information with different biological growth media. Also, database 40 may be used to store spectral profiles associated with different types of biological growth plates. Such spectral profiles, for example, may be used in the processing of biological growth plates, and may possibly aid in distinguishing area 58 (FIG. 2) associated with a biological agent relative to area 56 associated with a background. To generate such spectral profiles, the reflective response of exemplary biological growth media may be recorded via a spectrometer. Database 40 may store spectral profiles for a wide variety of different types of biological growth media, and database 40 may be updated from time to time with spectral profiles associated with new types of biological growth media.

More specifically, the spectral profiles associated with biological growth plates may aid in determining whether errors or defects exist in the biological media. Spectral profiles may be compared to measured data on the biological growth medium in order to identify manufacturer defects or use defects that render the biological growth media inaccurate. In this case, if the measured reflectance values associated with a biological growth medium deviate too far from the expected spectral response, that medium may be flagged as including possible errors. Such errors, for example, may be due to aging, manufacturing defects, or improper use by the lab technician or other user. For example, improper or excessive inoculation on a biological growth medium may cause the biological growth medium to be overfilled with inoculants, possibly causing errors that can be detected by comparison of measured reflectance values to expected spectral profiles associated with the biological media.

Each type of biological growth plate may define a unique spectral signature. If measured reflectance values in one or more areas do not match the expected values, as defined by the unique spectral signature, the medium may be flagged as including possible errors. In this way, biological growth media may be processed based on the spectral profiles in order to improve the integrity of the automated analysis of biological growth media. The spectral profiles might be used for other purposes, in addition to checking for clear errors due to aging, manufacturing defects or improper inoculation.

Figure 4:
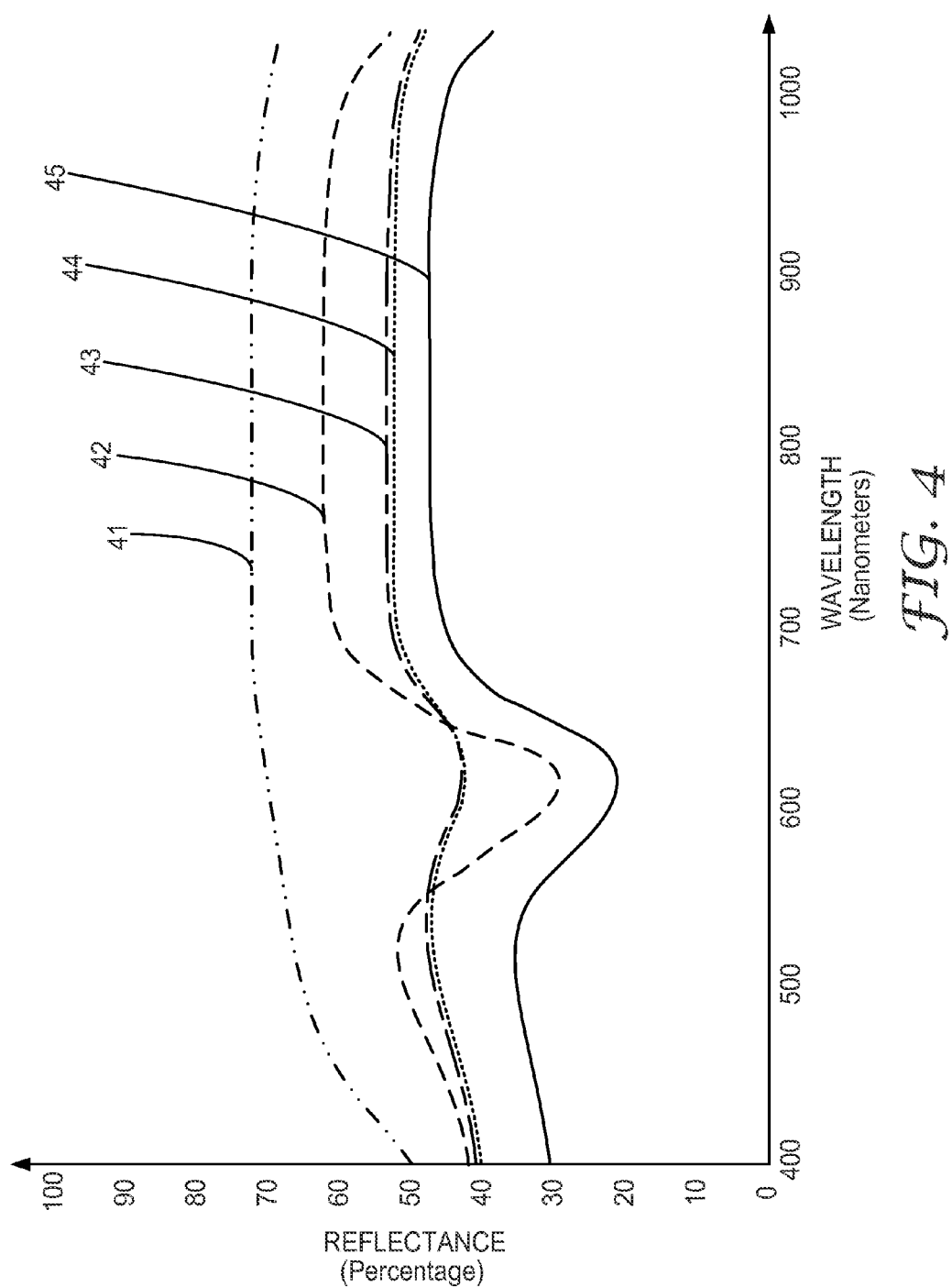
FIG. 4 is a graph illustrating the spectral response associated with different locations on a biological growth medium.

FIG. 4 is a graph illustrating the spectral response associated with different locations on a biological growth medium. The graph of FIG. 4 provides a rough illustration of data gathered in an experiment performed with respect to a PETRIFILM Yeast and Mold Count Plate, hereinafter, referred to as "PETRIFILM YM Plate", commercially available from 3M Company of Saint Paul Minn. The PETRIFILM YM Plate was inoculated with mold (M6 Strain) and incubated according to the specification of the PETRIFILM YM Plate. An Ocean Optics model number USB4000 spectrometer was used to measure reflectivity of the PETRIFILM YM Plate under a Halogen light source.

Five different locations on the PETRIFILM YM Plate were identified for comparisons of the spectral responses at different wavelengths. Line 41 corresponds to the spectral response associated with a background edge location (i.e., a first background location) on the PETRIFILM YM Plate. Line 42 corresponds to the spectral response associated with a biological agent (i.e., a first agent) formed on the PETRIFILM YM Plate. Line 43 corresponds to the spectral response associated with a non-edge background location (i.e., a second background location) on the PETRIFILM YM Plate. Line 44 corresponds to the spectral response associated with another non-edge background location (i.e., a third background location) on the PETRIFILM YM Plate. Line 45 corresponds to the spectral response associated with another biological agent (i.e., a second agent) formed on the PETRIFILM YM Plate.

As can be seen from FIG. 4, the spectral information in the visible spectrum between 400 nanometers to 700 nanometers, and specifically between 500 and 700 nanometers, carries substantially all of the information that distinguishes lines 42 and 45 (corresponding to the biological agents) from lines 41, 43 and 44 (corresponding to different background locations). Furthermore, line 42 shows less reflectance than lines 43 and 44 in a substantial portion of the visible spectrum, but shows more reflectance than lines 43 and 44 at wavelengths above 700 nanometers. In wavelengths between 800 and 900 nanometers, all lines are approximately parallel.

These observations can allow for normalization techniques to be used. For example, measured spectral reflectance at wavelengths between 700 and 1000 nanometers, or more specifically between 800 and 900 nanometers, may be used to normalize the measured spectral reflectance in the visible spectrum between 400 and 700 nanometers. Expected or measured spectral characteristics of the biological growth medium in different ranges can be exploited by capturing first images of a biological growth medium under illumination at wavelengths in the visible spectrum (e.g., between approximately 500 and approximately 700 nanometers), and capturing second images of a biological growth medium under illumination at wavelengths outside the visible spectrum (e.g., between approximately 800 and approximately 900 nanometers).

Figure 5:
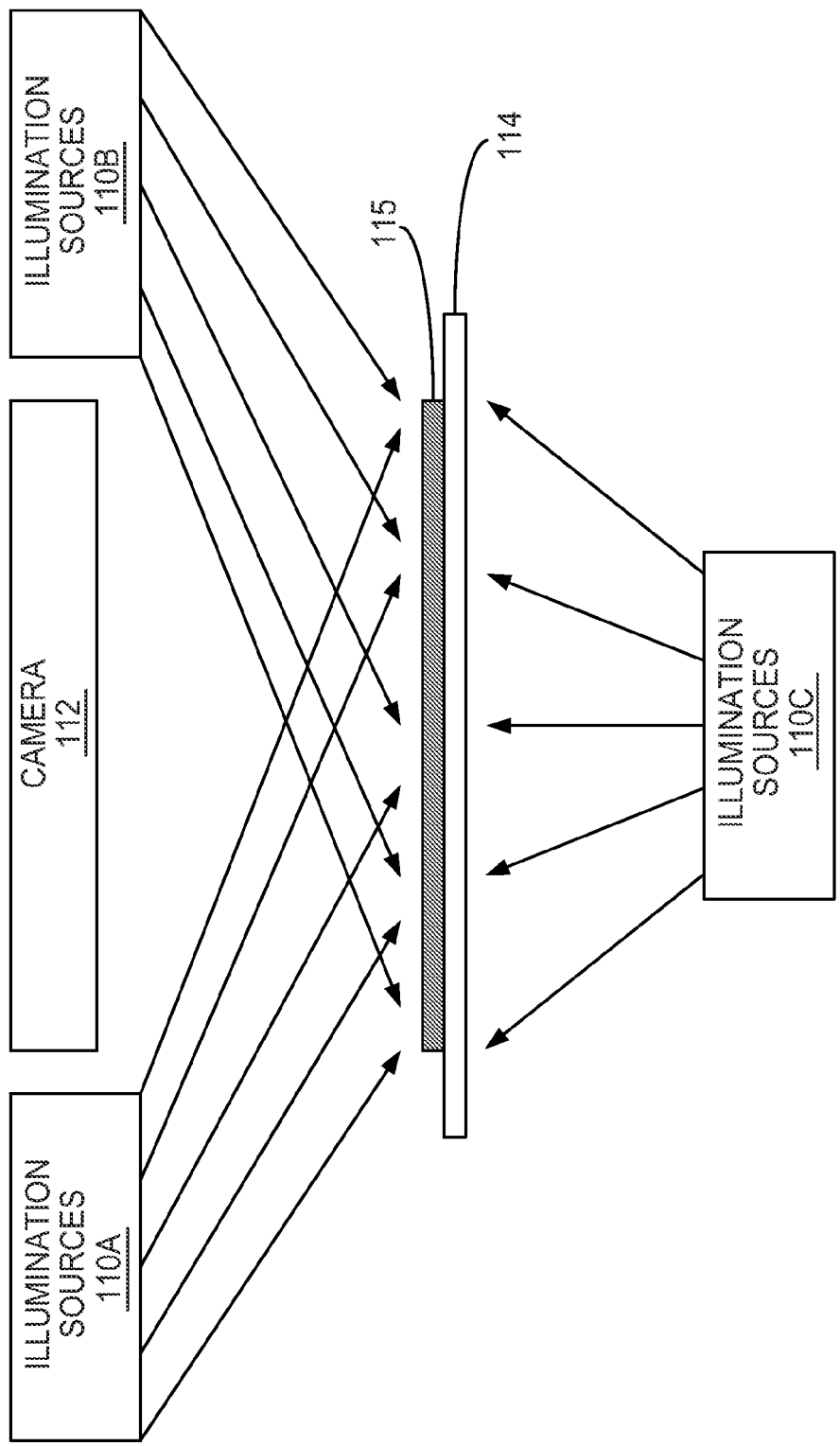
FIG. 5 is a block diagram illustrating the illumination of a biological growth medium within an illumination device.

FIG. 5 is a block diagram illustrating the illumination of a biological growth medium 115 within an illumination device, such as imaging unit 21 of FIG. 1. The illumination device includes illumination sources 110A, 110B and 110C (collectively illumination sources 110). The illumination device also includes a camera 112, which may comprise a 2-dimensional monochromatic camera or another type of camera. Biological growth medium 115 may be held in an imaging location relative to camera 112. Biological growth medium 115 may reside on a transparent platen 114, or could be held in place by guide mechanisms, pincers, or other elements with or without the need for platen 114.

Illumination sources 110 illuminate biological growth medium 115 with two or more different wavelengths of electromagnetic radiation, and camera 112 captures on or more images of biological growth medium 115 under each of these different illuminations. In particular, camera 112 may capture first images of biological growth medium 115 under illumination by illumination sources 110 with electromagnetic radiation in a first wavelength, e.g., light within the visible spectrum. Camera 112 may capture second images of biological growth medium 115 under illumination by illumination sources 110 with electromagnetic radiation in a second wavelength, e.g., light outside the visible spectrum. The first and second images may be captured when biological growth medium 115 is held in a fixed location relative to camera 112 to ensure that pixels of the first images correspond to pixels of the second images. These images can then be communicated from camera 112 to a computer for analysis.

The computer (not shown in FIG. 4) can analyze the images and create ratios for every pixel location to normalize the reflectance values of the first images. In particular, the ratio of spectral reflectance values in a second image relative to a first image can aid in detecting areas of biological growth medium 115 associated with a biological agents relative to areas of biological growth medium 115 associated with a background.

Illumination sources 110 may comprise any of a wide variety of devices or configurations. Illumination sources 110 may comprise florescent light sources with filters to define the proper wavelengths of illumination. Alternatively, illumination sources 110 may comprise semiconductor light sources, such as light emitting diodes. The light emitting diodes, for example, may be defined to create the wavelengths of illumination, or filters may be used for this purpose. Many other types of illumination sources could also be used. Although FIG. 5 shows illumination sources 110 positioned on the front side and backside of biological growth medium 115, illumination from only one side of biological growth medium 115 could be used in some cases. Indeed, a wide variety of configurations could be used to achieve two different wavelength ranges of illumination consistent with this disclosure.

In one example, illumination source 110A produces the illumination at the first wavelength and illumination source 110B produces the illumination at the second wavelength. Illumination source 110C may provide backlighting in the two different wavelengths. In other cases, each of illumination sources 110 may include elements capable of illuminating at the first and second wavelengths. Any number of different wavelength ranges may be used to define images under several different wavelengths of illumination. Upon capturing the images, camera 112 sends the images to a computer for image analysis consistent with this disclosure. Again, the first and second images may be captured when biological growth medium 115 is held in a fixed location relative to camera 112 to ensure that pixels of the first images correspond to pixels of the second images.

In another embodiment, white light illumination may be used with optical filters, either stationary or in a filter wheel. Also, in another embodiment white light illumination may be used with inserted optical filters on the image sensor in the form of a mask array, e.g., similar to a Bayer mask. In any case, the reflectance values of pixel locations in a first spectral image can be normalized based on the reflectance values for the same spatial pixel locations in one or more second spectral image. The first image may be associated with a different wavelength of illumination than the one or more second images. Additional images at different wavelengths of illumination may also be used.

Figure 6:
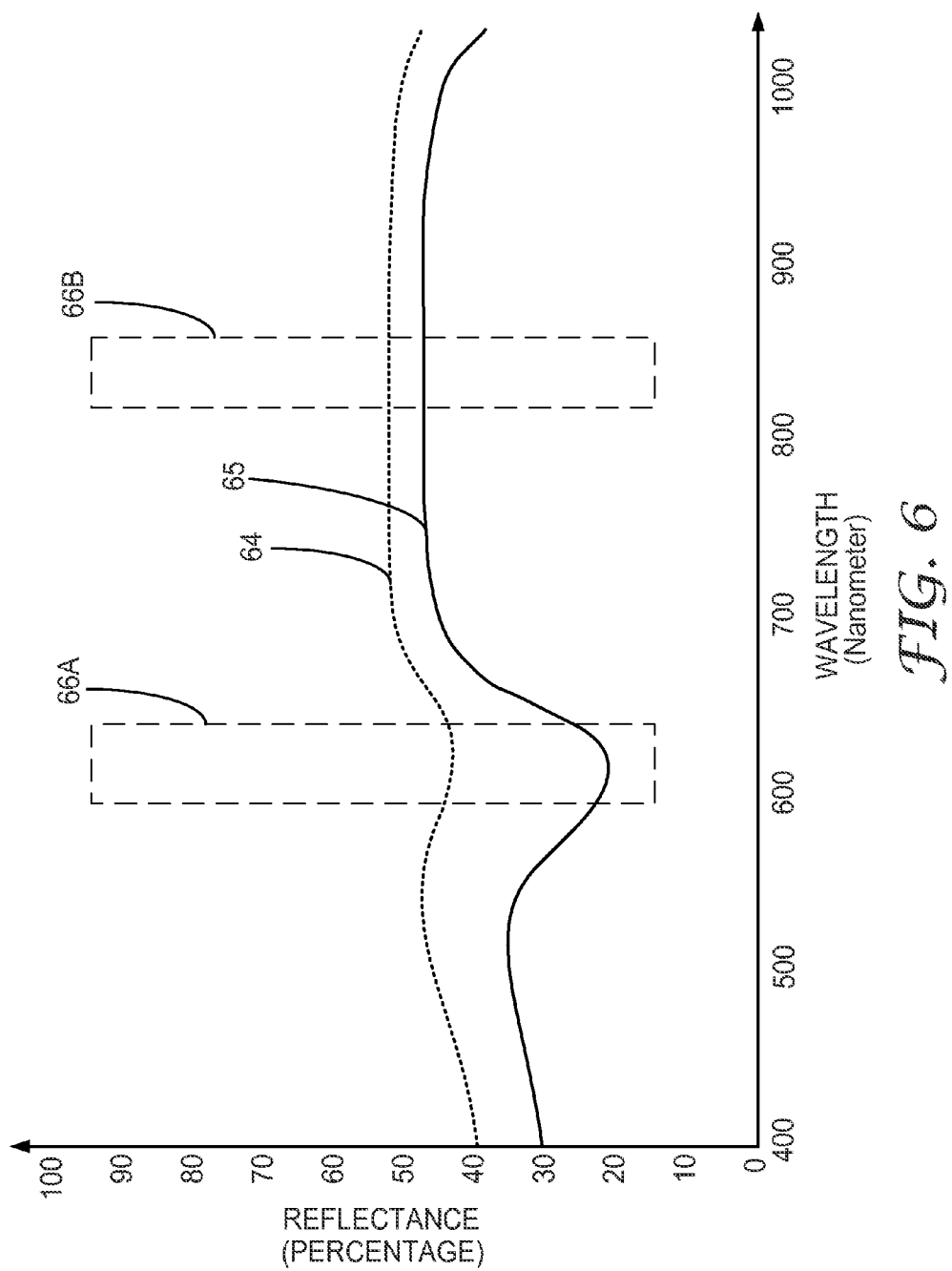
FIG. 6 is a graph illustrating the spectral response associated with a biological agent formed on a biological growth medium and the spectral response associated with a background area on the biological growth medium.

FIG. 6 is a graph illustrating the spectral response associated with an element formed on a biological growth medium and the spectral response associated with a background area on the biological growth medium. In FIG. 6, line 64 corresponds to line 44 of FIG. 4 and line 65 corresponds to line 45 of FIG. 4. Windows 66A and 66B may define the illumination wavelength ranges used to capture first images and second images respectively. For each of the images, the intensity of each pixel location may be determined, and a ratio of the intensities in windows 66A (associated with a first spectral image) and 66B (associated with a second spectral image) may be determined. This process may be viewed as normalizing the reflectance values of the first images associated with window 66A based on second images associated with window 66B. Such normalization by use of ratios can improve the ability to detect whether each given pixel is associated with a background or a biological agent. Furthermore, if desired, the expected spectral profile associated with backgrounds and agents may be programmed into the computer, and used to augment the analysis by providing expected values or expected ratios for pixels in the background and pixels associated with biological agents. In this way, expected spectral profiles may aid in identifying biological agents. As noted, the expected spectral profiles may also be used for quality control and detection of probably errors due to aging, manufacturing defects or improper inoculation.

The techniques of this disclosure may significantly improve the ability to differentiate background from biological agents. Even if the absolute differences between reflectance of background and biological agents in images generated under the first illumination are not significant, the normalized differences may be significant. Accordingly, the normalization techniques of this disclosure may yield improvements in the ability to differentiate or distinguish background regions from biological agents that form on the biological growth medium. At every pixel location (or possibly for sets of pixels within different areas), the ratios generated to normalize the first images may be compared to a threshold to determine whether that location corresponds to a biological agent or background. Other more complicated enumeration rules or techniques could also be applied to the calculated ratios at every pixel location (or at different areas defined by sets of pixel locations).

Figure 7:
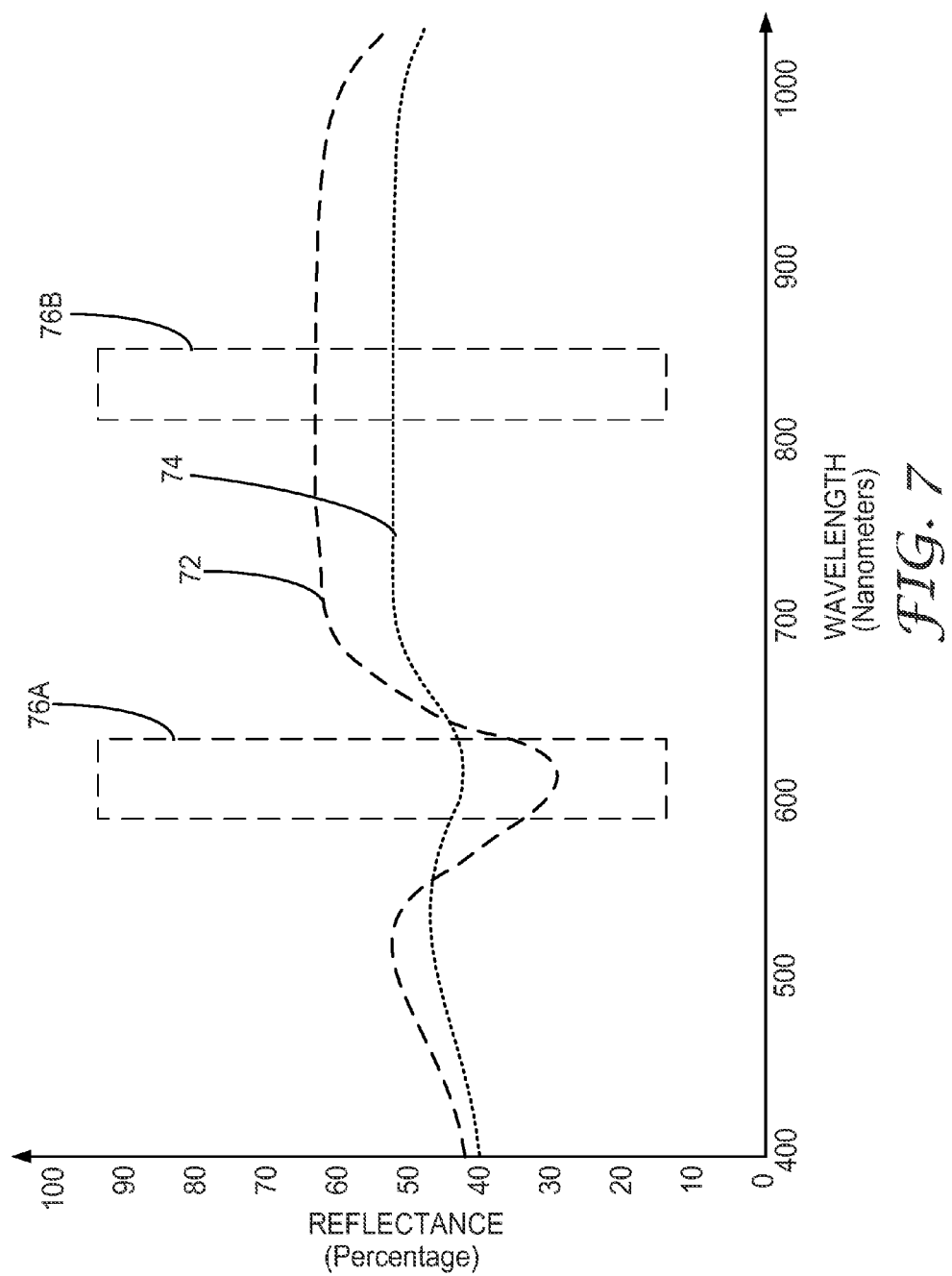
FIG. 7 is another graph illustrating the spectral response associated with a biological agent formed on a biological growth medium and the spectral response associated with a background area on the biological growth medium.

FIG. 7 is another graph illustrating the spectral response associated with an element formed on a biological growth medium and the spectral response associated with a background area on the biological growth medium. In FIG. 7, line 74 corresponds to line 44 of FIG. 4 and line 72 corresponds to line 42 of FIG. 4. Windows 76A and 76B may define the illumination used to capture first images and second images respectively. For each of the images, the intensity of each pixel location may be determined, and a ratio of the intensities in windows 76A and 76B may be determined. This process may be viewed as normalizing the spectral reflectance values of the first images associated with window 76A based on spectral reflectance values of the second images associated with window 76B. The ratios, then, can be compared to one or more thresholds to determine whether the pixel locations correspond to biological agents or to background.

As with the example of FIG. 6, this normalization by use of ratios can improve the ability to detect whether each given pixel is associated with a background or a biological agent. Again, if desired, the expected spectral profile associated with backgrounds and agents may be programmed into the computer, and used to augment the analysis by providing expected values or expected ratios for pixels in the background and pixels associated with biological agents.

In the example of FIG. 7, the ability to differentiate background (associated with line 74) from biological agents (associated with line 72) may be improved significantly relative to an absolute comparison of values in one frequency range (e.g., defined by first window 76A). In this case, even thought the absolute differences between reflectance of background and biological agents in window 76A for images generated under the first illumination are only about fifteen percent, the normalized differences may be over thirty percent. Accordingly, the example of FIG. 7, the use of normalization techniques or ratios as outlined herein, may yield more than 100 percent improvements in quantified differences of pixels associated with a biological agent relative to pixels in the background.

Figure 8:
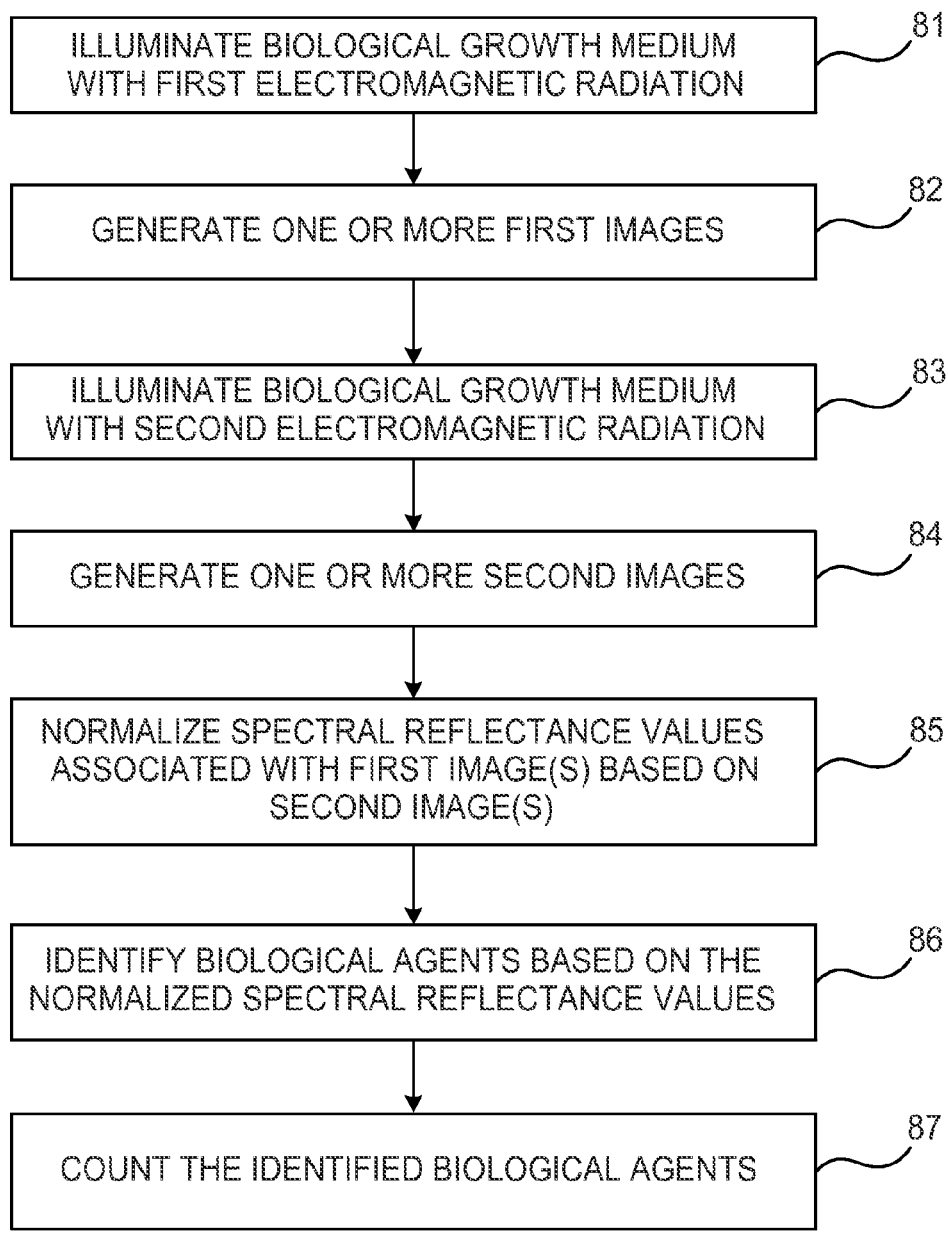
FIGS. 8-9 are flow diagrams illustrating techniques of this disclosure.

FIG. 8 is a flow diagram illustrating a technique consistent with this disclosure. As shown in FIG. 8, imaging unit 21 illuminates biological growth medium 24 with first electromagnetic radiation (as shown in step 81), and generates one or more first images of biological growth medium 24 illuminated with the first electromagnetic radiation (as shown in step 82). Imaging unit 21 also illuminates biological growth medium 24 with second electromagnetic radiation (as shown in step 83), and generates one or more second images of the biological growth medium illuminated with the second electromagnetic radiation (as shown in step 84). The generated images may be sent to computer 22 for image analysis.

Computer 22 counts biological agents on biological growth medium 24 based on the first and second images. In particular, computer 22 normalizes spectral reflectance values in the one or more first images based on the one or more second images (as shown in step 85), identifies the biological agents based on the normalized spectral reflectance values (as shown in step 86), and counts the identified biological agents (as shown in step 87). Put another way, computer 22 determines ratios of spectral reflectance values in the one or more first images to spectral reflectance values in the one or more second images, identifies the biological agents based on the ratios, and counts the identified biological agents.

The first electromagnetic radiation may be within a visible spectrum, and the second electromagnetic radiation may be outside the visible spectrum. For example, the first electromagnetic radiation may comprise light having a wavelength between approximately 500 and 700 nanometers, and the second electromagnetic radiation may comprise light having a wavelength between approximately 800 and 900 nanometers. If desired computer 22 may store a spectral profile associated with the biological growth medium, in which case the identification of biological agents on biological growth medium 24 may be based on the first and second images and the stored spectral profile. Alternatively, the stored spectral profiles may be used to process the biological growth medium, possibly providing a quality check on the biological growth medium. Computer 22 may be updated with new spectral profiles, as new types of biological growth plates are developed.

Figure 9:
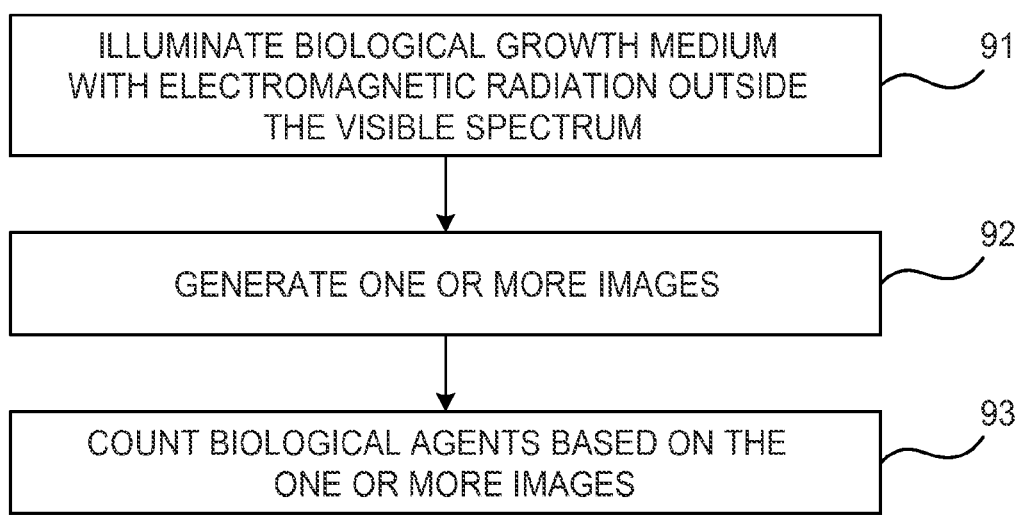

FIG. 9 is another flow diagram illustrating a technique consistent with this disclosure. As shown in FIG. 9, imaging unit 21 illuminates biological growth medium 24 with electromagnetic radiation outside a visible spectrum (as shown in step 91), and generates one or more images of biological growth medium 24 illuminated with the electromagnetic radiation outside the visible spectrum (as shown in step 92). The generated images may be sent to computer 22 for image analysis, and computer 22 may count biological agents on biological growth medium 24 based on the one or more images (as shown in step 93).

Again, the electromagnetic radiation that is outside the visible spectrum may comprise light having a wavelength between approximately 700 and approximately 1000 nanometers, and more specifically between approximately 800 and approximately 900 nanometers. Images within the visible spectrum may also be generated, in which case, computer 22 may count biological agents on biological growth medium 24 based on one or more first images associated with illumination in the visible spectrum, and one or more second images associate with illumination outside the visible spectrum.

The techniques described herein may be subject to a wide variety of modifications and implementation-specific details. For example, the use of images generated under light outside the visible spectrum may find other applications, such as with biological growth media designed to manifest spectral information in wavelengths outside the visible spectrum. In addition, although specific exemplary systems have been described, the techniques of this disclosure could be used in other types of systems or devices, such as modular biological growth media processing systems, or fully integrated biological readers that include imaging and image processing capabilities.

The techniques described herein may be implemented in hardware, software, firmware, or any combination thereof. If implemented in software, the techniques may be realized at least in part by a computer-readable medium comprising instructions that, when executed by computer of a biological growth medium processing system, cause the computer to perform one or more of the techniques of this disclosure. The computer-readable data storage medium may form part of a computer program product, which may include packaging materials. The computer-readable medium may comprise random access memory (RAM) such as synchronous dynamic random access memory (SDRAM), read-only memory (ROM), non-volatile random access memory (NVRAM), electrically erasable programmable read-only memory (EEPROM), FLASH memory, magnetic or optical data storage media, and the like.

The computer-readable instructions may be executed in the computer of the system by one or more processors, general purpose microprocessors, ASICs, FPGAs, or other equivalent integrated or discrete logic circuitry. Accordingly, the term "processor," as used herein may refer to any structure suitable for implementation of the techniques described herein.

For software embodiments, this disclosure may provide a computer-readable medium comprising instructions that upon execution in a computer of a biological growth medium processing system cause the computer to receive one or more images of the biological growth medium, the one or more images having been generated during illumination of the biological growth medium with the electromagnetic radiation outside the visible spectrum, and count biological agents on the biological growth medium based on the one or more images.

In addition, this disclosure may provide a computer-readable medium comprising instructions that upon execution in a computer of a biological growth medium processing system cause the computer to receive one or more first images of the biological growth medium, the one or more first images having been generated during illumination of the biological growth medium with first electromagnetic radiation, receive one or more second images of the biological growth medium, the one or more second images having been generated during illumination of the biological growth medium with second electromagnetic radiation, normalize spectral reflectance values in the one or more first images based on the one or more second images, and count the biological agents based on the normalized spectral reflectance values.

If implemented in hardware, this disclosure may be directed to a circuit, such as an integrated circuit, ASIC, FPGA, logic, or various combinations thereof configured to perform one or more of the techniques described herein. Various modifications may be made without departing from the spirit and scope of the invention. These and other embodiments are within the scope of the following claims.

The invention claimed is:

1. A method comprising:
   illuminating the biological growth medium with first electromagnetic radiation that is within the visible spectrum;
   generating one or more first images of the biological growth medium illuminated with the first electromagnetic radiation;
   illuminating a biological growth medium with second electromagnetic radiation that is outside a visible spectrum;
   generating one or more second images of the biological growth medium illuminated with the second electromagnetic radiation;
   normalizing spectral reflectance values in the one or more first images based on the one or more second images;
   identifying biological agents based on the normalized spectral reflectance values; and counting the biological agents.

2. The method of claim 1, further comprising:
   determining ratios of spectral reflectance in the one or more first images to spectral reflectance in the one or more second images;
   identifying the biological agents based on the ratios; and counting the identified biological agents.

3. The method of claim 1, further comprising:
   storing a spectral profile associated with the biological growth medium; and
   processing the biological growth medium based on the stored spectral profile.

4. A method comprising:
   illuminating a biological growth medium with first electromagnetic radiation;
   generating one or more first images of the biological growth medium illuminated with the first electromagnetic radiation;
   illuminating the biological growth medium with second electromagnetic radiation;
   generating one or more second images of the biological growth medium illuminated with the second electromagnetic radiation;
   normalizing spectral reflectance values in the one or more first images based on the one or more second images, wherein normalizing spectral reflectance values in the one or more first images based on the one or more second images comprises determining ratios of spectral reflectance values in the one or more first images to spectral reflectance values in the one or more second images for different pixel locations;
   identifying the biological agents based on the normalized spectral reflectance values wherein identifying the biological agents comprises comparing the ratios to one or more thresholds; and
   counting the identified biological agents.

5. The method of claim 4, wherein the first electromagnetic radiation is within a visible spectrum, and the second electromagnetic radiation is outside the visible spectrum.

6. The method of claim 4, further comprising:
   storing a spectral profile associated with the biological growth medium; and
   processing the biological growth medium based on the stored spectral profile.

7. A system comprising:
   an imaging unit that illuminates a biological growth medium with electromagnetic radiation that is outside a visible spectrum, and generates one or more images of the biological growth medium illuminated with the electromagnetic radiation outside the visible spectrum;
   wherein the imaging unit illuminates the biological growth medium with first electromagnetic radiation that is within the visible spectrum, generates one or more first images of the biological growth medium illuminated with the first electromagnetic radiation, illuminates the biological growth medium with second electromagnetic radiation that is outside the visible spectrum, and generates one or more second images of the biological growth medium illuminated with the second electromagnetic radiation; and
   a computer that counts the biological agents on the biological growth medium based on the one or more images;
   wherein the computer counts the biological agents on the biological growth medium based on the first and second images of the biological growth medium;
   wherein the computer normalizes spectral reflectance values in the one or more first images based on the one or more second images;
   wherein the computer identifies the biological agents based on the normalized spectral reflectance values;
   wherein the computer counts the identified biological agents.

8. The system of claim 7, wherein the imaging unit illuminates the biological growth medium with light having a wavelength between approximately 700 and approximately 1000 nanometers.

9. The system of claim 7, wherein the computer:
   stores a spectral profile associated with the biological growth medium; and
   processes the biological growth medium based on the stored spectral profile.

10. A system comprising:
    an imaging unit that illuminates a biological growth medium with first electromagnetic radiation, generates one or more first images of the biological growth medium illuminated with the first electromagnetic radiation, illuminates the biological growth medium with second electromagnetic radiation, and generates one or more second images of the biological growth medium illuminated with the second electromagnetic radiation; and
    a computer that normalizes spectral reflectance values in the one or more first images based on the one or more second images, identifies the biological agents based on the normalized spectral reflectance values, and counts the identified biological agents;
    wherein the computer normalizes spectral reflectance values in the one or more first images based on the one or more second images by determining ratios of spectral reflectance values in the one or more first images to spectral reflectance values in the one or more second images for different pixel locations;
    wherein the computer identifies the biological agents by comparing the ratios to one or more thresholds.

11. The system of claim 10, wherein the first electromagnetic radiation is within a visible spectrum, and the second electromagnetic radiation is outside the visible spectrum.

12. The system of claim 10, wherein the computer:
    stores a spectral profile associated with the biological growth medium; and
    processes the biological growth medium based on the stored spectral profile.

13. A system comprising:
    means for illuminating a biological growth medium with first electromagnetic radiation;
    means for generating one or more first images of the biological growth medium illuminated with the first electromagnetic radiation;

means for illuminating the biological growth medium with second electromagnetic radiation;
means for generating one or more second images of the biological growth medium illuminated with the second electromagnetic radiation;
means for normalizing spectral reflectance values in the one or more first images based on the one or more second images;
means for identifying the biological agents based on the normalized spectral reflectance values; and
means for counting the identified biological agents.

* * * * *